(12) United States Patent
Reser et al.

(10) Patent No.: US 9,808,370 B1
(45) Date of Patent: Nov. 7, 2017

(54) ANTI-SNORING PILLOW

(71) Applicants: Richard E. Reser, Tiffin, OH (US); Todd Sarka, Tiffin, OH (US)

(72) Inventors: Richard E. Reser, Tiffin, OH (US); Todd Sarka, Tiffin, OH (US)

( * ) Notice: Subject to any disclaimer, the term of this patent is extended or adjusted under 35 U.S.C. 154(b) by 0 days.

(21) Appl. No.: 15/456,713

(22) Filed: Mar. 13, 2017

Related U.S. Application Data

(60) Provisional application No. 62/307,525, filed on Mar. 13, 2016.

(51) Int. Cl.
*A61F 5/56* (2006.01)
*A47G 9/10* (2006.01)
*A47C 7/38* (2006.01)

(52) U.S. Cl.
CPC .............. *A61F 5/56* (2013.01); *A47G 9/1045* (2013.01); *A47G 9/1081* (2013.01); *A47C 7/383* (2013.01); *A47G 2009/1018* (2013.01)

(58) Field of Classification Search
CPC .............. A47G 9/10; A47G 2009/1018; A47G 9/1081; A47G 9/109; A47C 7/38; A47C 7/383; A61F 5/56
USPC ............................................. 5/636, 637, 640
See application file for complete search history.

(56) References Cited

U.S. PATENT DOCUMENTS

| | | | | |
|---|---|---|---|---|
| 4,748,702 A * | 6/1988 | Sandler | ..................... | A61F 5/56 128/848 |
| 4,850,067 A * | 7/1989 | Latorre | ..................... | A47G 9/10 5/636 |
| 5,920,932 A * | 7/1999 | Hershgordon | ........... | A47G 9/10 5/490 |
| 7,100,227 B2 * | 9/2006 | Frisbee | ..................... | A61F 5/56 5/490 |
| 7,546,651 B2 * | 6/2009 | Groteke | ..................... | A61F 5/56 5/636 |
| 8,566,985 B2 * | 10/2013 | Kim | ..................... | A47G 9/109 5/636 |
| 8,650,684 B1 * | 2/2014 | Mackinnon | ........ | A61G 13/1215 5/637 |
| 8,677,531 B2 * | 3/2014 | Popitz | ................... | A47G 9/1081 5/630 |
| 2004/0172760 A1 * | 9/2004 | Frisbee | ..................... | A61F 5/56 5/636 |
| 2006/0260055 A1 * | 11/2006 | Frisbee | ..................... | A61F 5/56 5/636 |
| 2008/0163428 A1 * | 7/2008 | Groteke | ..................... | A61F 5/56 5/638 |

(Continued)

*Primary Examiner* — Robert G Santos
(74) *Attorney, Agent, or Firm* — Jerry Semer

(57) ABSTRACT

The invention is a pillow that positions the neck enabling the sleeper to keep his airways open and get a good night's rest without snoring. The invention is a rectangular block of foam with a center cavity for an individual's head. The pillow is contoured to allow the lordotic curve of the cervical spine to be maintained and ensures that the upper portion of the thoracic spine is properly supported. Over the neck a foam bridge is formed to hold the jaw firmly in place whether a person lays on his back or sides. The bridge keeps the mandible from opening during sleep prohibiting mouth-breathing and snoring. Both the pillow and the bridge are made of flexible foam that is flexible enough to allow the neck to pass through the opening in the bridge. The bridge is position to keep the mouth closed and the airway open ensuring no snoring.

8 Claims, 5 Drawing Sheets

(56) References Cited

U.S. PATENT DOCUMENTS

Figure 1:
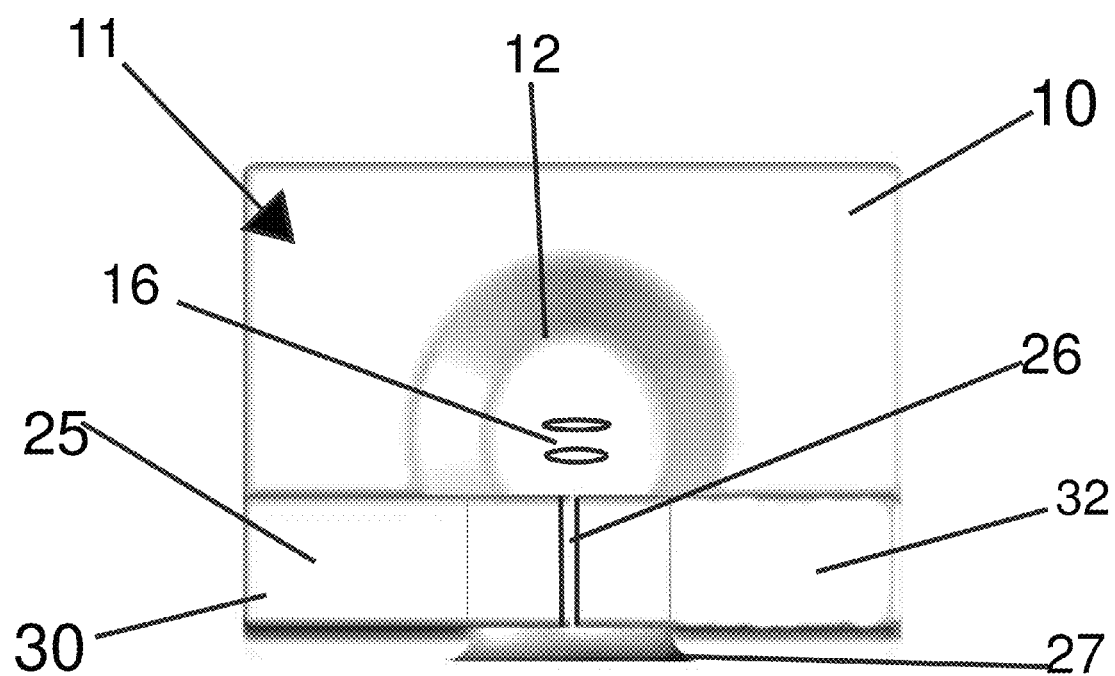

| | | | |
|---|---|---|---|
| 2011/0094033 A1* | 4/2011 | Lee | A61F 5/56 5/636 |
| 2012/0060846 A1* | 3/2012 | Leoniak | A61F 5/56 128/845 |
| 2012/0180220 A1* | 7/2012 | Popitz | A47G 9/1081 5/638 |
| 2013/0047339 A1* | 2/2013 | Kim | A47G 9/109 5/637 |
| 2015/0265075 A1* | 9/2015 | Liu | A61F 5/56 5/640 |
| 2017/0173297 A1* | 6/2017 | Park | A61M 21/00 |

* cited by examiner

ANTI-SNORING PILLOW

FIELD OF THE INVENTION

This invention relates to the field of anti-snoring pillows and more particularly to a pillow that holds the neck shoulder and back in proper cervical position and gently holds the mouth closed to eliminate snoring while an individual sleep.

BACKGROUND OF THE INVENTION

Snoring is a common problem among all ages and both genders. Snoring is noisy breathing during sleep. It affects approximately 90 million Americans adults. Snoring may occur nightly or intermittently. Persons most at risk are males and those who are overweight, but snoring is a problem of both genders. Snoring usually becomes more serious as people age. It can cause disruptions to your own sleep and also your bed-partner's sleep. It can lead to fragmented and un-refreshing sleep which translates into poor daytime function (tiredness and sleepiness). The two most common adverse health effects are daytime dysfunction and heart disease.

While you sleep, the muscles in the throat relax. The tongue falls backward, and the throat becomes narrow and "floppy." As you breathe the walls of the throat begin to vibrate. These vibrations are the characteristic sound of snoring. The narrower your airway becomes, the greater the vibration and the louder your snoring. Sometimes the walls of the throat collapse completely which create a condition called apnea (cessation of breathing). This is a serious condition which requires medical attention.

Snoring can lead to sever unpleasant symptoms which includes: excessive daytime sleepiness, morning headaches, weight gain, awakening in the morning not feeling rested, change in your level of attention, concentration, or memory. These common symptoms not only occur to the person snoring but also to the bed partner.

There have been many attempts in the art to solve the problem of snoring. These attempts arrange from sleep apnea machines to mouthpieces, chin straps, pillows, etc. The inventor has developed a pillow to help individuals stop snoring. There are many pillows on the market that are designed somewhat to stop snoring. These pillows are designed to modify an individual's behavior while he sleeps by ensuring that he does not sleep on his back. Ideally, sleeping on your side should lessen the effects of snoring. Snoring usually occurs when an individual rolls over on his/her back during sleep. The anti-snore pillows are typically shaped in such a way as to ensure that an individual sleeps on either side and not his back.

The inventor has taken a different approach. With the inventors pillow an individual can sleep on either side or his back. The inventor being a chiropractor began by designing a pillow that no matter what position you sleep in either on your back or your side the pillow will place your neck, head and shoulders in the proper cervical position. The pillow is designed with an indention for cradling the head, neck and face. This indention cradles the neck in a bio-posturally correct position easing discomfort and keeping the airway of the sleeper open. The neck is supported and the spine is aligned which allows a refreshing night sleep.

The pillow also has a bridge that fits over the neck. Beneath the cavity in the pillow is a bridge. This bridge extends up from the neck area of the pillow and extends over the neck of the individual with his head in the cavity on the pillow. The top of the bridge that extends over the neck is made out of foam so that it easily bends and has an opening so that the individual can places his/her head in cavity of the pillow and place the extensions of the bridge over his/her neck. This bridge gently holds the mandible from opening during sleep prohibiting mouth-breathing.

The idea behind bridge is very simple and that's why the bridge is so effective: the bridge holds the jaw firmly in place. This reduces the chance of your tongue falling back into the throat and blocking the airways. The holding of the jaw also reduces the risk of loose-tissue, centered on the neck and jaw, from vibrating. Without the bridge the mouth is open and the soft palate constricts the airway leading to vibration and snoring. The bridge is position to keep the mouth closed and with the mouth closed this airway remains opening and there is no snoring. The bridge is design so that it will keep the mouth closed no matter what position the individual lays in the indention in the pillow.

The person can lay on either size or on his back and the bridge will still hold the mouth closed. The pillow with the bridge and the proper positioning of the neck enable a sleeping individual to keep is airways open and get a good night's sleep without snoring.

DETAILED DESCRIPTION OF THE DRAWINGS

Figure 2:
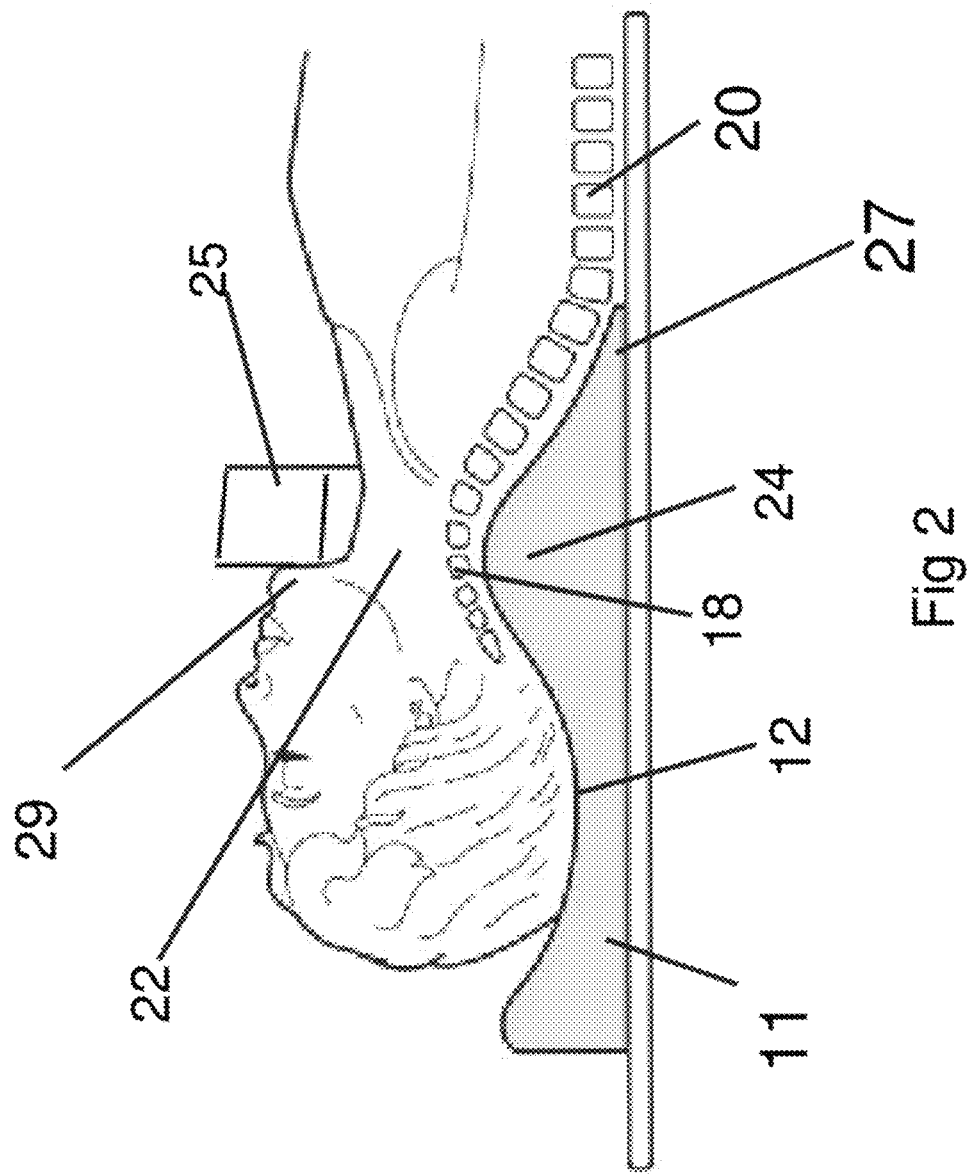
Figure 3:
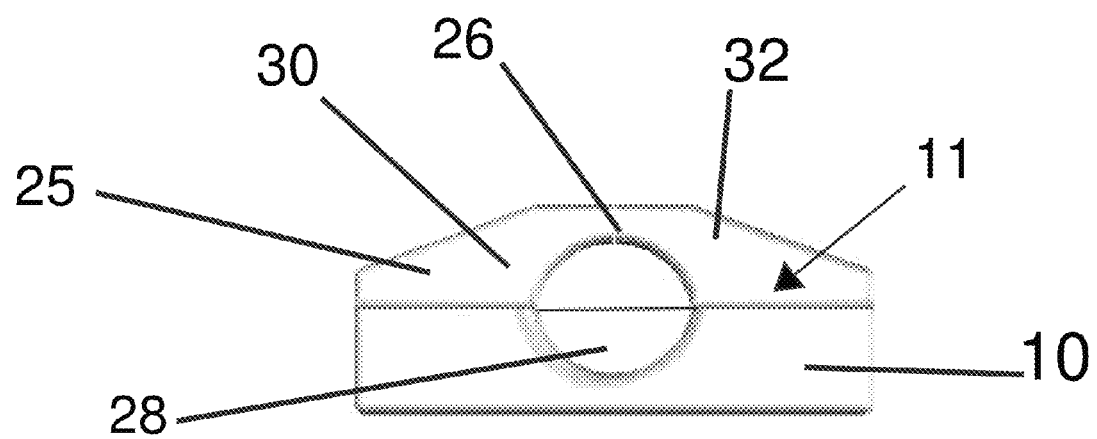
Figure 4:
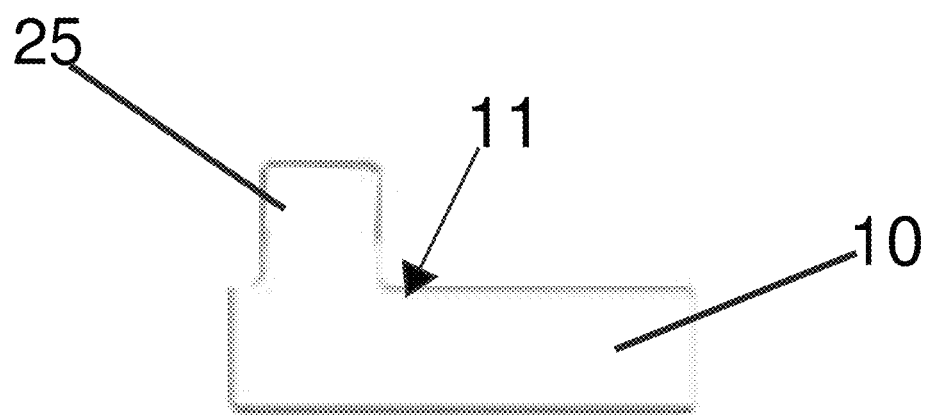
Figure 5:
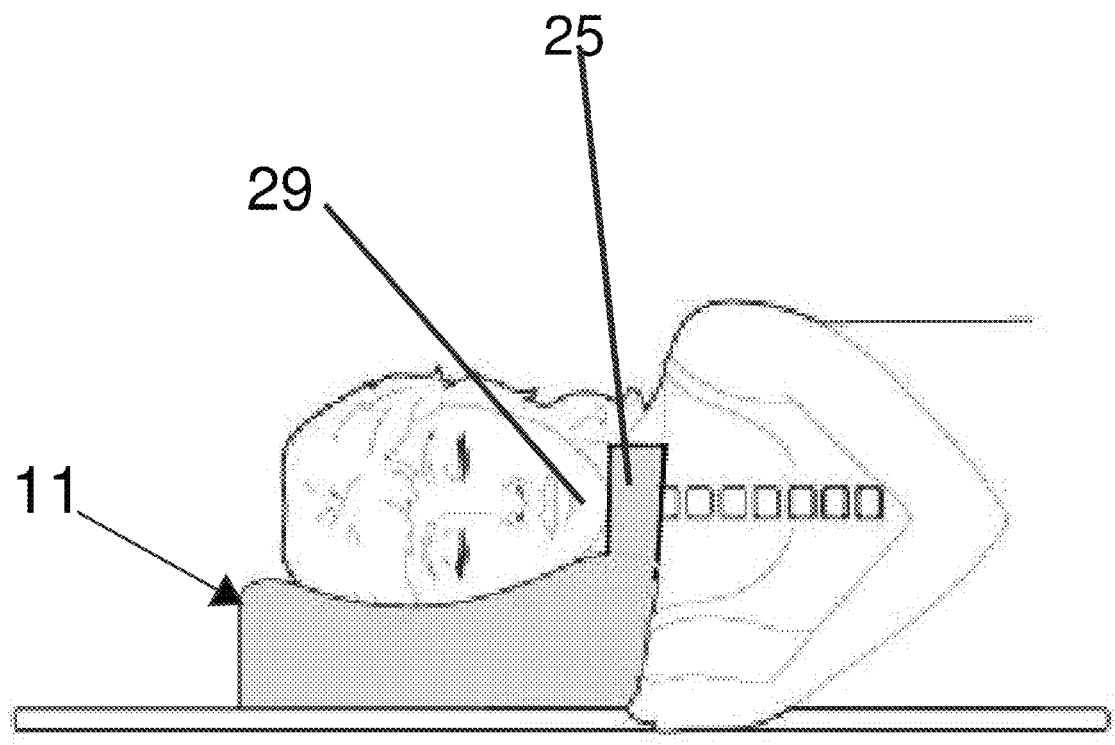

FIG. 1 is a top view of the pillow.
FIG. 2 is a cutaway view of the pillow with an individual lying on his back with his head in the central cavity.
FIG. 3 is a front view of the pillow.
FIG. 4 is a side view of the pillow.
FIG. 5 is a cutaway view of the pillow with an individual lying on his side with his head in the central cavity.

SUMMARY OF THE INVENTION

The invention is a pillow that properly positions of the neck and holds the mouth closed enabling a sleeping individual to keep is airways open and get a good night's sleep without snoring. The invention is comprised of a rectangular shaped block of foam with a center cavity where an individual resting on his back lays his head. In this position the head is safely cradled. The contour of the pillow as one move from the central cavity downward to the bottom of the pillow, moves upward under the neck to form a mound and then it tapers down forming a slight wedge at the bottom of the block of foam. This allows the lordotic curve of the cervical spine to be maintained and ensures that the upper portion of the thoracic spine is properly supported. Over the neck a foam bridge is formed to holding the jaw firmly in place. The bridge gently keeps the mandible from opening during sleep prohibiting mouth-breathing and snoring.

The bridge with the block of foam forms a large opening in the front of the pillow through which the individuals neck passes when the head is in the central cavity. There is an opening in the center of the bridge that splits the bridge in two parts. An individual when he is placing his head in center cavity passes his neck through the opening. Both the pillow and the bridge are made of flexible foam. The bridge's two parts are flexible enough to allow the neck to pass through the opening and then the two parts flex back into place holding the jaw firmly in place.

An individual can also lay on either side on the pillow. An individual who wishes to lay on his side places his head in center cavity and passes his neck through opening in the center of the bridge. The sides of the bridge flex enough that the neck can pass through opening allowing the flexible sides of the bridge to lay on the individual's neck. The bridge for a person lying on his side just as with the individual lying on his back holds the jaw firmly in place keeping the individual's mouth closed.

The idea behind the pillow is that the bridge gently holds the mandible from opening during sleep prohibiting mouth-breathing. The bridge holds the jaw firmly in place. This reduces the chance of your tongue falling back into the throat and blocking the airways and reduces the risk of loose-tissue, centered on the neck and jaw, from vibrating. Without the bridge, the mouth is open and the soft palate constricts the airway leading to vibration and snoring. The bridge is position to keep the mouth closed, the airway open ensuring no snoring. The bridge is design so that it will keep the mouth closed no matter what position the individual lays in the central cavity of the pillow. The pillow with the bridge properly positions the neck enabling a good night's sleep without snoring.

DETAILED DESCRIPTION OF THE PREFERRED EMBODIMENT

The invention is a pillow 11. The pillow 11 is a block of foam 10 shown in FIG. 1. In the preferred embodiment the block of foam 10 is rectangular in shape. The block of foam 10 has a center cavity 12 where an individual resting on his back lays his head 14. In this position the head is safely cradled. Ridges 16 can be located underneath the head which allow for air flow. The contour of the pillow as it moves to the neck allows the lordotic curve 18 of the cervical spine 20 to be maintained and as the block of foam 10 tapers down to a slight wedge 26, the upper portion of the thoracic spine is properly supported. This is shown in FIG. 2.

FIG. 2 shows the central cavity 12 with the head 14 resting within that cavity. The central cavity 12 of the block of foam 10 as you move towards the bottom or along the neck 22 moves upward from the center cavity 12 forming a mound 24 under the neck 22. This allows the lordotic curve of the cervical spine to be maintained. The mound 24 then moves downward towards the bottom of the block of foam 10 forming a slight wedge 27. The mound 24 with wedge 27 properly supports the thoracic spine. Also in FIG. 2, over the neck 22 is a portion of bridge 25 holding the jaw 29 firmly in place. The bridge 25 gently keeps the mandible from opening during sleep prohibiting mouth-breathing and snoring.

FIG. 1 is a top view of the pillow 11. It shows the block of foam 10 with the center cavity 12. At the bottom of the block of foam 10 is the bridge 25. At the very bottom and in the center of the block of foam 10 FIG. 1 shows the wedge 27. In FIG. 1 the mound 24 is hidden by bridge 25. Bridge 25 as it passes over mound 24 has an opening 26 that completely cuts bridge 25.

FIG. 3 is the front view of the pillow 11. In FIG. 3 one can see the block of foam 10 and the bridge 25. In FIG. 3 the block of foam attaches to the bridge 25 forming a large opening 28. This large opening 28 is where the individuals neck passes under the bridge when an individual is a lying on the pillow with his head 14 in the central cavity 12. One can see that opening 26 passes completely through bridge 25 forming a right side piece 30 and a left side piece 32 of bridge 25. The bridge is made of a similar foam to the block of foam 10. Left side piece 32 and right side piece 30 are flexible. An individual when he is placing his head in center cavity 12 passes his neck through opening 26. Left side piece 32 and right side piece 30 are flexible enough that the neck can pass through opening 26 and flexible piece 32 and 30 then lay upon the individual's neck 22.

FIG. 4 shows a side view of the pillow 11. FIG. 4 shows the block of foam 10. At the bottom of block of foam 10 is bridge 25.

FIG. 5 is a cutaway view of an individual lying on his side with his head 14 lying in the central cavity 12. The individual lays on the block of foam 10 in the central cavity 12. The bridge 25 as with the individual lying on his back holds the jaw 26 firmly in place keeping the individuals mouth closed. The bridge 25 gently keeps the mandible from opening during sleep prohibiting mouth-breathing and snoring.

An individual who wishes to lay on his side when he is placing his head 14 in center cavity 12 passes his neck through opening 26. Left side piece 32 or right side piece 30 are flexible enough that the neck can pass through opening 26 and flexible piece 32 and 30 then lay upon the individual's neck 22.

The idea behind the pillow 11 is that the bridge 25 gently holds the mandible from opening during sleep prohibiting mouth-breathing. The bridge holds the jaw firmly in place. This reduces the chance of your tongue falling back into the throat and blocking the airways. The holding of the jaw 29 also reduces the risk of loose-tissue, centered on the neck and jaw, from vibrating. Without the bridge 25 the mouth 24 is open and the soft palate constricts the airway leading to vibration and snoring. The bridge 25 is position to keep the mouth 24 closed and with the mouth 24 closed this airway remains opening and there is no snoring. The bridge 25 is design so that it will keep the mouth 24 closed no matter what position the individual lays in the central cavity 12 in the pillow 11. The person can lay on either size or on his back and the bridge 25 will still hold the mouth 24 closed. The pillow 11 with the bridge 25 properly positioning of the neck enabling a sleeping individual to keep his airways open and get a good night's sleep without snoring.

We claim:

1. An anti-snoring pillow for an individual comprising:
   a) pillow with a front end and a central cavity with a center; and,
   b) a contoured area from the central cavity to the front end starting in the center of the central cavity moves upward to form a mound and then tapers down forming a slight wedge at the front end of the pillow; and,
   c) a bridge passing substantially horizontally over the mound forming an opening with the mound; and,
   d) an opening in the center of the bridge that splits the bridge into two bridge side pieces; and,
   e) the bridge is configured through the bridge's contact with a front of an individual's mandible to hold the individual's mandible firmly in place keeping a individual's mouth closed when an individual's head is in the central cavity.

2. The anti-snoring pillow as in claim 1 wherein:
   a) the pillow is made of flexible foam.

3. The anti-snoring pillow as in claim 1 wherein:
   a) the bridge is configured to allow an individual's neck to pass thereunder when the individual's head is in the central cavity.

4. A The anti-snoring pillow as in claim 1 wherein:
   a) the contoured area is configured to support an upper portion of an individual's thoracic spine.

5. The anti-snoring pillow as in claim 2 wherein:
   a) the bridge is configured to allow an individual's neck to pass thereunder when the individual's head is in the central cavity.

6. The anti-snoring pillow as in claim 5 wherein:
a) the contoured area is configured to support an upper portion of an individual's thoracic spine.
7. The anti-snoring pillow as in claim 2 wherein:
a) the two bridge side pieces are adapted to be flexible enough that the individual's neck can pass through the opening in the bridge; and,
b) whereas when the individual places his head in center cavity, his neck passes through the opening in the center of the bridge and the two bridge side pieces flex back and lay upon the individual's neck.
8. The anti-snoring pillow as in claim 6 wherein:
a) the two bridge side pieces are adapted to be flexible enough that the individual's neck can pass through the opening in the bridge; and,
b) whereas when the individual places his head in center cavity, his neck passes through the opening in the center of the bridge and the two bridge side pieces flex back and lay upon the individual's neck.

* * * * *